United States Patent [19]
Campine et al.

[11] Patent Number: 6,080,554
[45] Date of Patent: Jun. 27, 2000

[54] METHODS AND COMPOSITIONS FOR USE IN CHARACTERIZING MULTIPLE SCLEROSIS DISEASE ACTIVITY IN A SUBJECT

[75] Inventors: Isabelle Willie Luce Campine, Heverlee; Kenny Leo De Meirleir, Mechelen, both of Belgium; C. V. Taylor Herst, Oakland, Calif.

[73] Assignee: R.E.D. Laboratories, N.V., Zellik, Belgium

[21] Appl. No.: 09/300,814

[22] Filed: Apr. 27, 1999

[51] Int. Cl.⁷ .............................. C12Q 1/42; C12Q 1/37; C12Q 1/00
[52] U.S. Cl. ................... 435/21; 435/24; 435/23; 435/4; 435/975
[58] Field of Search .................. 435/21, 24, 23, 435/4, 975

[56] References Cited

U.S. PATENT DOCUMENTS 5,866,119  2/1999  Bandman et al. ........................ 435/4

FOREIGN PATENT DOCUMENTS

98/15646  4/1998  WIPO .

OTHER PUBLICATIONS

Charachon, Guillaume, et al., "Phosphorothioate Analogues (2'–5')(A)$_4$: Agonist And Antagonist Activities In Intact Cells," *Biochemistry* (1990) vol. 29:2550–2556.

Suhadolink, Robert J., et al., "Biochemical Evidence For A Novel Low Molecular Weight 2–5A–Dependent Rnase L In Chronic Fatigue Syndrome," *Journal Of Interferon And Cytokine Research* (1997) vol. 17:377–385.

Suhadolink, Robert J., et al., "Upregulation Of The 2–5A Synthetase/RNase L Antiviral Pathway Associated With Chronic Fatigue Syndrome," *Clinical Infectious Diseases* (1994) vol. 18, (Suppl 10:S96–S104.

Suhadolink, Robert J., et al., "Changes In The 2–5A Synthetase/RNase 1 Antiviral Pathway in A Controlled Clinical Trial With Poly(I)–Poly($C_{12}$U) In Chronic Fatigue Syndrome," *In Vivo* (1994) vol. 8:599–604.

*Primary Examiner*—Louise N. Leary
*Attorney, Agent, or Firm*—Bret E. Field; Bozicevic, Field & Francis LLP

[57] ABSTRACT

Methods are providing for characterizing multiple sclerosis disease activity in a subject. In the subject methods, a sample is obtained from a subject suspected of having or known to have multiple sclerosis. The sample is then assayed for the presence of both high and low molecular proteins having RNAse L activity and a ratio of these two proteins is derived. The resultant ratio is then used to characterize the MS disease activity in the subject, e.g. to confirm an initial MS diagnosis, to determine the stage of the disease, to monitor disease progression, to predict disease attacks, and the like. Also provided by the subject invention are kits for practicing the methods.

18 Claims, No Drawings

METHODS AND COMPOSITIONS FOR USE IN CHARACTERIZING MULTIPLE SCLEROSIS DISEASE ACTIVITY IN A SUBJECT

TECHNICAL FIELD

The field of this invention is multiple sclerosis.

BACKGROUND OF THE INVENTION

Multiple sclerosis (MS) is a neurological illness of unknown etiology associated with attacks of focal or multifocal neurological dysfunction arising from lesions within the central nervous system (CNS). In America and Northern Europe, MS is the most common neurological disease, with prevalence rates estimated between 50–100 per 100,000 population. The onset of disease is most common in early adulthood. Recurrent attacks can occur over many years, with approximately 30 percent of the patients progressing to a severe form of the disease which can be fatal.

MS is pleomorphic in its presentation. The clinical manifestations are determined in part by the location of the foci of demyelination within the CNS. Classical features of the disease include impaired vision, nystagmus, dysarthria, ataxia and intention tremor, and weakness/paralysis of one or more limbs.

The most common form of the disease is episodic. Symptoms develop with subsequent recovery, then another attack occurs. In approximately 50 percent of all patients with MS, attacks become more frequent, usually with a worsening of symptomatology. In 30 percent of all patients, the disease develops into what is referred to as "progressive/relapsing," the most severe form of the disease. In this state remissions are rare and patients frequently become wheelchair bound.

The characterization of MS disease activity (including diagnosis, determination of disease state, monitoring of disease progression, prediction of disease attacks, and the like), remains problematic. To aid the clinician, the only laboratory test available is testing the cerebrospinal fluid for oligoclonal bands, present in approximately 90 percent of all patients. Examination of the brain for demyelinating plaques, using magnetic resonance imaging (MRI) is useful but expensive, and is not warranted except in a small group of patients in which all other clinical and laboratory tests are negative. Furthermore, there is no diagnostic laboratory test to determine if a patient is having an "attack," to monitor the progress of the "attack," to determine if the patient is progressing to a more active form of the disease (i.e., progressive/relapsing). Finally, there is no laboratory test available as a prognostic indicator and/or capable of monitoring the course of therapy. One commentator has summarized the situation as follows: "The need for reliable markers of disease activity in multiple sclerosis (MS) to better guide basic research, diagnosis, treatment, and monitoring therapy is well-recognized." Laman et al., Mult. Scler. (June 1998) 4:266–269.

As such, there is a need in the field to develop additional means for characterizing MS disease activity in a subject.

Relevant Literature

A review of multiple sclerosis is provided in Harrison's Principles of Internal Medicine (McGraw-Hill, 1998) pp 2409–2418.

WO 98/15646, as well as Suhadolnik et al., J. Interferon & Cytokine Res. (1997) 17: 377–385 disclose a 37 kDa protein having RNAse L enzyme activity, as well as its use in the diagnosis of Chronic Fatigue Syndrome (CFS).

SUMMARY OF THE INVENTION

Methods and compositions are provided for characterizing MS disease activity in a subject. In the subject methods, a sample is obtained from a subject suspected of having or known to have MS. The sample is then assayed for the presence of both high and low molecular proteins having RNAse L activity. The presence and relative amounts of these high and low molecular weight proteins are then employed to characterize the MS disease activity in the patient, e.g. to confirm an initial diagnosis, to determine a disease state, to monitor disease progression, to predict a disease attack, etc. Also provided by the subject invention are kits for practicing the subject methods.

DESCRIPTION OF THE SPECIFIC EMBODIMENTS

Methods and compositions are provided for characterizing multiple sclerosis (MS) disease activity in a subject. In the subject methods, a sample is obtained from a subject suspected of having or known to have MS. The sample is then assayed for the presence of both high and low molecular proteins having RNAse L activity. The results of this assay are then compared to reference values and the MS disease activity in the subject is characterized. Also provided are kits for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

As summarized above, the subject invention provides a method of characterizing the MS disease activity in a subject suspected of having, or known to have, MS. Subjects suspected of having, or known to have, MS and thus amenable to the subject methods can be identified using any convenient protocol. One convenient protocol is diagnosis based on clinical symptoms. A number of different clinical symptoms may be used to identify subjects that may have or have MS. These clinical symptoms include: weakness of the limbs; sensory symptoms, e.g. paresthesia or hypesthesia; ataxia; optic neuritis; diplopia; trigeminal neuralgia; facial paralysis; vertigo; urinary or bowel movement abnormalities; and cognitive dysfunction, e.g. memory loss, impaired attention, problem-solving difficulties, slowed information processing, and difficulty in shifting between cognitive tasks. The presence of one or more of the above symptoms may be used to identify subjects suspected of suffering from MS. Other assays may also be employed, including MRI imaging, the oligoclonal band assay described in greater detail infra, etc.

The first step of the subject methods is to obtain a suitable sample from the subject or patient of interest, i.e. a patient suspected of having or known to have MS. The sample may be derived from any initial source that comprises the high and low molecular weight proteins having RNAse L activity (if present). In many embodiments, the sample is derived from cells that comprise the high and low molecular weight proteins of interest, if present—i.e. if the patient from which the cells are derived has MS. In other embodiments, the sample may be derived from fluids into which the proteins of interest have been released, e.g. are present. In many embodiments, a suitable initial source for the patient sample is blood. As such, the sample employed in the subject assays is generally a blood derived sample. The blood derived sample may be derived from whole blood or a fraction thereof, e.g. serum, plasma, etc., where in many embodiments the sample is derived from blood cells harvested from whole blood. Of particular interest as a sample source are mononuclear cells. As such, a preferred sample is one that is derived from peripheral blood mononuclear cells (PBMCs).

In these preferred embodiments in which the sample is a PBMC derived sample, the sample is generally a fluid PBMC derived sample. Any convenient methodology for producing a fluid PBMC sample may be employed. In many embodiments, the fluid PBMC derived sample is prepared by: (a) separating PBMCs from whole blood, i.e. collecting PBMCs, e.g. by centrifugation (such as by Ficoll-Hypaque density gradient centrifugation); (b) disrupting the collected cells, e.g. by contacting with a lysing buffer; (c) and removing the resultant cellular debris to obtain a cell-free extract, e.g. by centrifugation. A representative means for producing a suitable fluid PBMC derived sample, i.e. a fluid PBMC extract, is disclosed in WO 98/15646, the disclosure of which is herein incorporated by reference.

Once the patient derived sample is obtained, it is assayed for the presence of both high and low molecular weight proteins having RNAse L activity. The high molecular weight protein has a molecular weight ranging from about 75 to 85, usually 77 to 83 and specifically about 80 kDa, as determined under SDS-PAGE reducing conditions. This protein is disclosed in Bisbal, et al., "Cloning and characterization of a RNase L inhibitor: a new component of the interferon-regulated 2–5A pathway," J. Biol. Chem (1995) 270: 13308–13317. The low molecular weight protein having RNAse L activity has a molecular weight ranging from about 30 to 40, usually from about 35 to 40 and specifically of about 37 kDa, as determined under SDS-PAGE reducing conditions. This protein is disclosed in Suhadolnik et al, "Biochemical evidence for a novel low molecular weight 2-5A-dependent RNase L in chronic fatigue syndrome," J Interferon Cytokine Res. (July, 1997) 17(7):377–85. See also WO 98/15646, the disclosure of which is herein incorporated by reference.

The sample may be assayed for the presence of the high and low molecular weight proteins having RNAse L activity using any convenient methodology. Generally, such methodology involves the following two steps: (a) fractionation of the sample in a manner sufficient such that the high and low molecular weight proteins are present in different fractions, i.e. separating the high and low molecular weight proteins from each other; and (b) detection of the high and low molecular weight proteins in the specific fractions, i.e. assaying each fraction for the presence or absence of the a protein having RNAse L activity, where the detection may be qualitative, semi-quantitative or quantitative, and is usually at least semi-quantitative (i.e. not just qualitative).

Fractionation may be accomplished using any convenient methodology, where the fractionation technique may or may not preserve the RNAse L activity of the protein. In other words, the fractionation technique employed may or may not employ native or non-denaturing conditions. Whether fractionation is carried out under denaturing or non-denaturing conditions depends on the particular manner in which the high and low molecular weight RNAse L proteins are detected, where representative detection methods are described in greater detail below.

Where the detection method is based on the detection of RNAse L activity, the sample may be fractionated using any convenient methodology which preserves the activity of the high and low molecular weight proteins. As such, fractionation is accomplished under non-danaturing conditions. Typically, the non-denaturing conditions are "native" conditions. By "native conditions" is meant fractionation by a process that substantially preserves the activity of the RNAse L species in the sample. Native conditions are those conditions that do not denature proteins, particularly enzymes. A variety of non-denaturing fractionation means are known to those of skill in the art, where one means of interest is gel filtration high performance liquid chromatography. Alternatively, where the detection method assays for just the presence of an RNAse L protein but not RNAse L activity, fractionation may be carried out under non-native, e.g. denaturing conditions, such as SDS-PAGE (sodium dodecylsulfate-polyacrylamide gel electrophoresis). As the fractionating step involves separating the high molecular weight protein from the low molecular weight protein, fractionation results in the production of a first fraction that putatively contains the low molecular protein (i.e. is suspected of containing the low molecular weight protein) and a second fraction that putatively contains the high molecular weight protein (i.e. is suspected of containing the high molecular weight protein).

As discussed above, following fractionation of the sample, the fractions are assayed for the presence of RNAse L proteins, either the high or low molecular weight protein. A number of assay protocols are know in the art for detecting RNAse L proteins. Suitable assays that may be employed include: (1) the core-cellulose assay, as described in Silverman et al., Anal. Biochem. (1985) 144: 450–460; (2) the ribosomal cleavage assay, as described in Suhadolnik et al., Clin. Infect. Dis. (1994) 18: S96–S104; (3) assaying for the hydrolysis of a labeled RNAse L substrate, e.g. poly(U)-3'-[$^{32}$P]pCp in the presence of $p_3A_3$; (4) the photolabeling/immunoprecipitaton/fractionation assay, as described in Suhadolnik et al, "Biochemical evidence for a novel low molecular weight 2-5A-dependent RNAse L in chronic fatigue syndrome," J Interferon Cytokine Res. (July, 1997) 17(7):377–85; and the like. Each of the above assays is further described in WO 98/15646, the disclosure of which is herein incorporated by reference.

Of particular interest in many embodiments is an assay having the following steps: covalently labeling any RNAse L proteins present in the sample; followed by (2) fractionation of the sample by SDS-PAGE and detection of the covalent label. The covalent label employed in this assay is a label that is capable of specifically and covalently binding to RNAse L proteins, where the label may comprise any convenient detectable moiety, such as a directly detectable moiety, e.g. a fluorescent or isotopic moiety, or an indirectly detectable moiety, such as a member of a more complex signal producing system (e.g. biotin). In many embodiments, the label will be an isotopic label, e.g. as found in $(2'-5')(A)_4 3'[^{32}P]pCp$. A reoresentative protocol for this type of assay is disclosed in Charachon, Biochemistry (1990) 29:2550–56. See also the Experimental Section, infra.

In addition to the above assays, antibody based assays may also be employed to determine the presence of the markers of interest in the patient sample being tested. Antibody body based assays require the use of antibodies specific for the protein markers described above, i.e. the high and low molecular weight RNAse L proteins.

Antibodies that specifically bind to the subject RNAse L proteins can be prepared using a variety of convenient methods known to those of skill in the art. See Guide to Protein Purification, supra, as well as Antibodies, A Laboratory Manual (Harlow & Lane eds., Cold Spring Harbor Press)(1988). The antibodies may be polyclonal or monoclonal antibodies depending on the nature of the intended use, as long as they are specific for one of the forms of RNAse L to the exclusion of the other form, so as to be capable of distinguishing between the two forms.

For preparation of polyclonal antibodies, the first step is immunization of the host animal with an RNAse L protein, where the RNAse L protein will preferably be in substantially pure form, comprising less than about 1% contaminant. The immunogen may comprise complete RNAse L, fragments or derivatives thereof. To increase the immune response of the host animal, the RNAse L may be combined with an adjuvant, where suitable adjuvants include alum, dextran, sulfate, large polymeric anions, oil & water emulsions, e.g. Freund's adjuvant, Freund's complete adjuvant, and the like. The RNAse L may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The RNAse L is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for RNAse L is to immunize a suitable host, where suitable hosts include rats, hamsters, mice and the like, and are preferably mice. The RNAse L immunogen, which as above may be the entire RNAse L protein or a fragment or derivative thereof, is administered to the host in any convenient manner, where such methods include: subcutaneous injection with adjuvants, nitrocellulose implants comprising RNAse L, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available and known to those of skill in the art. The plasma and myeloma cells are fused by combining the cells in a fusion medium usually in a ratio of about 10 plasma cells to 1 myeloma cell, where suitable fusion mediums include a fusion agent, e.g PEG 1000, and the like. Following fusion, the fused cells are selected, e.g. by growing on HAT medium. Following hybridoma cell production, culture supernatant from individual hybridomas is screened for reactivity with RNAse L using standard techniques, where such screening techniques include ELISA, dot blot immunoassays and the like. The antibody may be purified from the supernatants or ascites fluid by conventional techniques, e.g. affinity chromatography RNAse L bound to an insoluble support, protein A sepharose and the like.

The above prepared antibodies may be modified in a number of different ways to optimize their utility for use in a particular immunoassay. For example, antibody fragments, such as Fv, F(ab')$_2$ and Fab may be prepared by cleavage of the intact protein, e.g. by protease or chemical cleavage. The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provided for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In immunoassays of the subject invention, a number of different immunoassay formats are known in the art and may be employed. Representative assay formats include Western blots on protein gels or protein spots on filters, where the antibody is labeled as described above, as is known in the art. Other immunoassays include those based on a competitive formats, as are known in the art. One such format would be where a solid support is coated with RNAse L. Labeled antibody is then combined with the patient derived sample suspected to produce a reaction mixture which, following sufficient incubation time for binding complexes to form, is contacted with the solid phase bound RNAse L. The amount of labeled antibody which binds to the solid phase will be proportional to the amount of RNAse L in the sample, and the presence of RNAse L may therefore be detected. Other competitive formats that may be employed include those where the sample suspected of comprising RNAse L is combined with a known amount of labeled RNAse L and then contacted with a solid support coated with antibody specific for RNAse L. Such assay formats are known in the art and further described in both Guide to Protein Purification, supra, and Antibodies, A Laboratory Manual, supra. Sandwich-format assays may also be employed. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. The insoluble supports may be any compositions to which antibodies or fragments thereof can be bound, which is readily separated from soluble material, and which is otherwise compatible with the overall method of measuring RNAse L in the sample. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used. Samples, fractions or aliquots thereof are then added to separately assayable supports (for example, separate wells of a microtiter plate) containing support-bound allergen. Preferably, a series of standards, containing known concentrations of RNAse L is assayed in parallel with the samples or aliquots thereof to serve as controls. Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for RNAse L molecules to bind the insoluble first antibody. Generally, from about 0.1 to 3 hr is sufficient, usually 1 hr sufficing. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample. After washing, a solution containing the second RNAse L specific antibody is applied. The second antibody may be labeled, as described above, to facilitate direct, or indirect detection and/or quantification of binding. Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of RNAse L is present. An example is the use of a labeled antibody specific to the second antibody. The volume, composition and concentration of second antibody solution provides for measurable binding to the RNAse L already bound to the first antibody. Generally, the same volume as that of the sample is used: from about 0.001 to 1 ml is sufficient, usually about 0.1 ml sufficing. The concentration will generally be sufficient to saturate all RNAse L potentially bound to first antibody. The concentration generally will be about 0.1 to 50 µg/ml, preferably about 1 µg/ml. The solution containing the second antibody is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing. After the second antibody has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

In the subject methods, the fractions are at least assayed for the presence of the high and low molecular proteins. In some embodiments, qualitative results are sufficient. Thus, one may be interested in identifying the substantial absence of the 80 kDa protein and the presence of the low molecule marker. Alternatively, one may be interested in making a qualitative determination of the ratio of the low to high molecular protein. In many embodiments, the assays employed at least provide semi-quantitative detection of the high and low molecular weight proteins, and not just qualitative detection.

Based on the presence or absence of the high and low molecular weight proteins, and usually the semi-quantitative values obtained for each of the proteins, the MS disease activity in the subject from which the sample was derived is characterized. Characterization of MS disease activity according to the subject methods typically involves comparing the results obtained to a table or other source of predetermined values or reference values which provide information about the disease activity in the host, e.g. that positively or negatively correlate to the presence of MS, a particular stage of MS, and the like. For example, a table of values may be consulted in this step, where the table comprises representative values for the high and low molecular weight proteins as found in patients suffering from MS. The values may be presented in numerical form, in picture form (e.g. as bands on a gel), and the like. By comparing the observed values with these reference values, characterization of MS disease activity, e.g. confirmation of diagnosis, determination of disease state, etc., is readily made. In many embodiments, one looks at the amount of one of the RNAse L proteins, e.g. the low molecular weight RNAse L protein, in relation to the amount of the other RNAse L protein, e.g. the high molecular weight RNAse L protein, i.e. one derives a ratio of the two proteins. This ratio is then compared to reference list of ratios.

As summarized above, the subject methods are methods of characterizing MS disease activity in a host. The term characterizing is used broadly to refer to derivation of any type of information about the state of the MS disease in the host. As such, the subject methods may be used to confirm an initial diagnosis of MS disease, to determine the state of the disease in an MS patient, to monitor the progression of the disease, to predict the occurrence of an attack, and the like. Where the subject invention is employed to confirm an initial diagnosis, a sample is obtained from subject suspected of having MS (where the subject may be identified as described supra). The sample is assayed for the presence of the high and low molecular weight RNAse L forms, a ratio of the two is derived and then compared to reference values, where the reference values correlate given ratios to the presence or absence of MS.

The subject methods are also employed to determine the stage of the MS disease in the subject. In other words, the subject MS disease activity characterization methods may be employed to determine whether the MS patient is in the relapsing-remitting stage or in the chronic progressive stage of the disease. To determine the stage of the disease, the observed values for the high and low molecular weight proteins in the assayed sample are compared to reference values which are correlated to a particular stage of MS, e.g. remitting relapsing or chronic progressive.

In yet other embodiments, characterization of disease activity yields information concerning the disease progression in the patient, e.g. whether disease progression has accelerated or slowed. For example, the initial characterization date, i.e. the amount of high and low molecular forms in the patient derived sample, could be employed as a baseline value to evaluate subsequent testings, e.g. at some time following the initial testing, e.g. 3 months. If the amount of low molecular weight form decreases in subsequent testing, this indicates that the disease is not progressing. Alternatively, if the amount of low molecular weight form increases, this indicates that the disease is progressing in severity.

The characterization data obtained from the subject methods may also be used to determine whether a particular therapeutic regimen is having positive affects with respect to the progression of the disease. For example, at various time periods during the course of treatment, the subject methods may be performed to obtain a reading of the amount of high and low molecular weight forms of the RNAse L protein. If the amount of the low molecular weight marker is increasing, this indicates that the treatment regimen is not having the desired effect. Alternatively, if the amount of the low molecular weight marker is decreasing, this indicates that the treatment regimen is working.

In yet other embodiments, the characterization data obtained from the subject methods is used to predict when an MS attack may occur. In this embodiment, the characterization data is compared to reference values, where some of the reference values correlate to the occurrence of an attack.

Depending on the particular test protocol, the subject methods may further include an additional biochemical assay capable of identifying MS activity in the subject. An additional biochemical assay of interest is an assay which detects the presence of oligoclonal bands in cerebral spinal fluid (CSF). A variety of such assays are known to those of skill in the art and may be employed in the subject methods. See e.g. Mehta et al., Electrophoresis. (Mar 1988) 9(3):126–8; Mehta, et al., J Clin Lab Immunol. (July 1981)6(1):17–22; Trbojevic-Cepe et al., Neurologija. (1989)38(1):11–21; Lasne et al., J Neurochem. (May 1981)36(5):1872–4; Mehta et al., J Neurosci Methods. (Jun 1986) 16(4):277–82.

Also provided by the subject invention are kits for use in carrying out the subject methods. The kits at least comprise reagents necessary for carrying out the RNAse L detection assays, where such kits may include: RNAse L specific antibodies and/or immunoassay devices comprising the same; RNAse L binding agents, such as $(2'-5')(A)_4-3'[^{32}P]$ pCp; members of a signal producing system, such as antibodies, enzyme substrates, and the like; various buffers for use in carrying out the subject RNAse L detection assays; and the like. The kits may further include one or more reagents necessary for preparation of the patient derived sample, such as heparin, Ficoll-Hypaque, lysing buffer, protease inhibitor, and the like. In addition, the subject kits may further include one or more components employed in fractionation of the sample, such as an electrophoretic medium or precursors thereof, e.g. dried precursors of polacrylamide gels, one or more buffer mediums or components thereof, and the like. In most embodiments, the kits further include at least an information storage and presentation medium that contains reference data with which assay results may be compared in order to confirm the presence or absence of MS in the subject being assayed, i.e. reference data that includes various values of the high and low molecular weight RNAse L proteins and relates these values to the presence or absence of MS. The information storage and presentation medium may be in any convenient form, such as a printed information on a package insert, an electronic file present on an electronic storage medium, e.g. a magnetic disk, CD-ROM, and the like. The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of MS, such as one or more reagents from an assay designed to detect the presence of oligoclonal bands in CSF, e.g. immunoxification reagents (e.g. anti-IgG); labeling reagents, such as silver salts, and the like.

The following examples are offered by way of illustration and not by way of limitation.

EXPERIMENTAL

I. Analysis and Quantification of Low and High Molecular Weight RNase L Proteins and the Combined Activity Thereof in Cell Extracts from MS Patients and Healthy Controls Study subjects were 29 patients who had previously been diagnosed as fulfilling the diagnostic criteria for MS and 20 healthy controls. Patients and controls were selected from medical practices in Overpelt and Brussels, Belgium. At the time of blood sampling, patient symptoms were evaluated and recorded.

A. Procedures

1. Extraction

Peripheral blood mononuclear cells (PBMCs) were separated from heparinized blood (30 mLs) by Ficoll-Hypaque density gradient centrifugation. Briefly, the heparinized blood was layered onto 20 mLs of Ficoll-Hypaque (Boyum, Scandinavian Journal of Clinical Laboratory Investigation, 97: 1–109, 1968) at a density of 1.077 g/mL at 20 C. and centrifuged for 30 minutes at 500×g. The PBMC layer was removed and washed once with 5 volumes of phosphate buffered saline (PBS). The cells were then resuspended in 5 mLs of red blood cell lysing buffer (155 mM NH$_4$Cl, 10 mM NaHCO$_3$, 0.1 mM EDTA, pH 7.4), kept on ice for 5 minutes, then centrifuged for 5 minutes at 500×g. The resultant cell pellet was washed one time with 15 mLs of PBS and centrifuged for 5 minutes at 500×g. The resultant pellet must was then stored at less than −70 C. until the protein extraction procedure could be performed.

To extract the proteins from the cell pellet, the PBMCs were resuspended in a volume approximately 5–10 times the cell volume in the extract buffer (10 mM HEPES, pH 7.6, 90 mM KCl, 1.5 mM Mg(OAc)$_2$, 0.5% non-ionic detergent (such as Nonidet P-40 or Igepal CA-630, Sigma Chemical Corporation)). The extract buffer also contained a mixture of protease inhibitors to help stabilize the extract and impeded the action of proteases, i.e. the MiniComplete protease inhibitor cocktail (Boehringer-Mannheim) which contains aprotinin, leupeptin, pefabloc-SC and EDTA.

The extraction procedure was performed at 2–4 degrees C., holding the cell pellet-extraction buffer in ice water or on wet ice for 5 minutes. The cell pellet-buffer mix was then vortexed at medium speed for 2 minutes at room temperature to ensure complete solubilization of the cell membranes. The cell pellet-buffer mix was then placed at 2–4 C. for an additional 5 minutes. The final step was to centrifuge the cell pellet-buffer mix at high speed in a microcentrifuge (16,000×g) for 2 minutes. The supernatant containing the proteins of interest was collected and the cell pellet is discarded. All cell extracts were stored at −70 C. until further analysis could be performed.

2. Quantification

Quantification of protein in the patient cell extracts was performed using a standard commercially available procedure of a modified Bradford method (Bio-Rad Laboratories). Analysis of LMW and HMW RNase L Proteins was performed using a radiolabeled 2'-5'A trimer and SDS-PAGE as described by the method of Charachon et al. (Biochemistry 29:2550–2556, 1990), the entire disclosure of which is incorporated herein by reference. Briefly, 2'-5'A trimer was radiolabeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4 C. to form 2'5'A-$^{32}$pC-OX. This reaction mixture was subsequently equilibrated to pH 8.0 by the addition of NaOH. This oxidized molecule was used as the radiolabel in all subsequent reactions for RNase L protein analysis (referred to below as radiolabeled 2'5'A). The radiolabeled 2'5'A was incubated with 200 micrograms of cell extract at 2–4 C. for 15 minutes to allow the radiolabeled 2'5'A to interact with any 2'5'A-binding proteins present, such as RNase L (all species). The 2'-5'A radiolabel was then covalently attached to all RNase L species by the addition of cyanoborohydride (20 mM in 100 mM phosphate buffer, pH 8.0); the cyanoborohydride reduces the oxidized ribose forming a covalent attachment to any amino groups nearby. The reduction reaction was allowed to occur for 20 minutes at room temperature. SDS-PAGE sample buffer, including a tracking dye, was added to the samples and all samples were incubated at 95 C. for 5 minutes to reduce any disulfide bonds present.

The samples were then subjected to standard SDS-polyacrylamide gel electrophoresis using a 4 percent stacking gel and a 10 percent separating gel (Bisbal et al, European Journal of Biochemistry 179:595–602, 1989). The gel was electrophoresed until the tracking dye had migrated to the bottom of the gel. The gel was then dried and subjected to autoradiography. The autoradiographs were then analyzed by densitometry, and quantification of any and all RNase L species present was performed using specialized software (Amersham Pharmacia Biotech). The results (in Table 1) are expressed as the density (or relative amount) of 37 kDa LMW RNase L present divided by the density (or relative amount) of 80 kDa HMW RNase L present, multiplied by a constant factor of 10.

3. RNase L Activity 2-5A-dependent RNase L activity (referred to as the RNase L Activity Assay) was detected using a ribosomal RNA cleavage assay with detection of highly characteristic specific cleavage products (SCPs) according to the procedure of Suhadolnik et al., Clin. Infect. Dis. 18:S96–S104, 1994). Briefly, the patient cell extract (75 micrograms of total protein) was incubated with 140 micrograms of a cytoplasmic extract from an RNase L-deficient subclone of L929 cells (the source of the intact 28S and 18S ribosomal RNA substrate). The reaction was carried out at 30 C. for 60 minutes. RNA was then extracted from this reaction using an organic extraction of low pH phenol (pH=4.0) and chloroform. The resultant RNA was then denatured in the presence of formaldehyde and formamide and analyzed by electrophoresis with the inclusion of a tracking dye. Electrophoresis was performed in a 1.5% agarose gel until the tracking dye had migrated to the bottom of the gel. The RNA bands was detected by staining with ethidium bromide and visualized under UV light. A photographic image was recorded and analyzed by densitometry. The activity due to RNase L is expressed (in Table 1) as the ratio of the SCPs to the remaining substrate (28S+18S ribosomal RNA), multiplied by a constant value of 100. For a discussion see Wreschner et al., Nature 289:414–417 (1981), the entire disclosure of which is incorporated herein by reference.

TABLE 1

B. Results

| Patient # | Protein (37/80)*10 | Activity SCP/ (28 + 18)*100 | Diagnosis | Considered Positive if . . . Protein > 3.00 | Activity > 100 |
|---|---|---|---|---|---|
| OV-003 | 0.90 | 59.50 | MS-CP | | |
| OV-005 | 10.80 | 96.90 | MS-RR | P | |
| OV-006 | 0.60 | 49.40 | MS-RR | | |
| OV-007 | 1.30 | 61.60 | MS-RR | | |
| OV-008 | 0.10 | 45.20 | MS-RR | | |
| OV-009 | 1.10 | 27.80 | MS-RR | | |
| OV-011 | 0.10 | 55.80 | MS-RR | | |
| OV-012 | 0.80 | 40.90 | MS-RR | | |
| OV-013 | 13.00 | 368.50 | Active MS-CP | P | P |
| OV-014 | 1.60 | 106.10 | Active MS-CP | | P |
| OV-016 | 0.10 | 87.30 | MS-RR | | |
| OV-017 | 1.80 | 85.50 | MS-RR | | |
| OV-018 | 0.60 | 62.20 | MS-RR | | |
| OV-019 | 1.00 | 75.40 | MS-RR | | |
| OV-020 | 1.20 | 79.60 | MS-RR | | |
| OV-021 | 1.00 | 104.10 | MS-RR | | P |
| OV-022 | 5.90 | 83.00 | MS-RR | P | |
| OV-024 | 6.10 | 88.00 | MS-RR | P | |
| OV-025 | 3.40 | 119.50 | MS-RR | P | P |
| OV-026 | 11.00 | 90.40 | MS-RR | P | |
| OV-027 | 1.00 | 120.10 | MS-RR | | P |
| OV-028 | 1.10 | 58.60 | MS-RR | | |

TABLE 1-continued

B. Results

| Patient # | Protein (37/80)*10 | Activity SCP/ (28 + 18)*100 | Diagnosis | Considered Positive if... Protein > 3.00 | Activity > 100 |
|---|---|---|---|---|---|
| OV-029 | 8.80 | 110.70 | MS-RR | P | P |
| OV-031 | 0.80 | 79.40 | MS-CP | | |
| OV-033 | 0.20 | 38.00 | MS-RR | | |
| OV-034 | 3.70 | 491.20 | MS-RR | P | P |
| OV-035 | 7.20 | 162.40 | MS-RR | P | P |
| OV-036 | 248.00 | 255.30 | Active MS-CP | P | P |
| OV-037 | 4.70 | 179.20 | MS-RR | P | P |
| IC-011 | 0.10 | 42.50 | Healthy Control | | |
| IC-024 | 2.20 | 42.00 | Healthy Control | | |
| IC-028 | 1.30 | 43.90 | Healthy Control | | |
| IC-029 | 1.20 | 43.90 | Healthy Control | | |
| IC-034 | 2.70 | 93.30 | Healthy Control | | |
| IC-037 | 3.60 | 62.70 | Healthy Control | P | |
| IC-038 | 2.00 | 86.10 | Healthy Control | | |
| IC-039 | 0.30 | 58.00 | Healthy Control | | |
| IC-040 | 0.70 | 35.60 | Healthy Control | | |
| IC-053 | 2.60 | 76.00 | Healthy Control | | |
| IC-055 | 2.70 | 53.60 | Healthy Control | | |
| IC-059 | 1.10 | 47.60 | Healthy Control | | |
| IC-061 | 1.30 | 65.40 | Healthy Control | | |
| IC-065 | 1.50 | 37.60 | Healthy Control | | |
| IC-066 | 1.70 | 51.50 | Healthy Control | | |
| IC-069 | 0.70 | 50.30 | Healthy Control | | |
| IC-071 | 1.50 | 70.30 | Heathy Control | | |
| IC-072 | 0.70 | 55.90 | Healthy Control | | |
| IC-076 | 1.60 | 64.70 | Healthy Control | | |
| IC-081 | 2.70 | 53.10 | Healthy Control | | |

C. Analysis of Results

In the data are set forth in Table 1, the Protein Assay data are expressed as the "ratio of LMW to HMW protein, multiplied by a constant value of 10." The Activity Assay data are expressed as the "ratio of SCPs to remaining substrate (28S+18S ribosomal RNA), multiplied by a constant value of 100." The clinical diagnosis at the time of blood sampling is included. Utilizing a cut-off value of 3.00 in the Protein Assay, and 100.00 in the Activity Assay, the following results were obtained:

Active MS-CP was detected in 3/3 cases when using the cut-off criteria of one or the other Assay for analysis MS-CP was detected in 3/5 cases (3 active, 3/3; 2 stable, 0/2)

14 of 29 patients with MS were positive when using the criteria of one or the other Assay for analysis (11/29 positive by Protein Assay, 10/29 by Activity Assay; 7/20 when using both criteria)

1 of 20 controls was positive when using the criteria of one or the other Assay for analysis (1/20 positive by Protein Assay, 0/20 by Activity Assay; 0/20 when using both criteria)

It is evident from the above results and discussion that relatively simple and rapid methods are provided for characterizing MS disease activity in a subject are provided. With the subject methods, accurate diagnosis of the MS condition, as well the identification of the stage and/or progression of the MS condition, may be obtained. As such, the subject methods provide for more accurate treatment regimens. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of characterizing multiple sclerosis disease activity in a subject, said method comprising:
    (a) obtaining a sample from said subject;
    (b) determining the relative amounts of high molecular weight RNAse L to low molecular weight RNAse L in said sample; and
    (c) using said relative amounts to characterize the multiple sclerosis disease activity in said subject.

2. The method according to claim 1, wherein said high molecular weight RNAse L has a molecular weight of about 80 KDa under SDS-PAGE reducing conditions.

3. The method according to claim 1, wherein said low molecular weight RNAse L has a molecular weight of about 37 KDa under SDS-PAGE reducing conditions.

4. The method according to claim 1, wherein said sample is a blood derived sample.

5. The method according to claim 4, wherein said blood derived sample is derived from PBMCs.

6. The method according to claim 1, wherein said method is a method of confirming whether said subject suffers from MS.

7. A method of characterizing multiple sclerosis disease activity in a subject, said method comprising:
    (a) obtaining a PBMC derived sample from said subject;
    (b) determining the ratio of 80 KDa RNAse L to 37 KDa RNAse L in said sample; and
    (c) using said ratio to characterize multiple sclerosis disease activity in said subject.

8. The method according to claim 7, wherein said method further comprises identifying at least one symptom associated with multiple sclerosis in said subject prior to said determining step.

9. The method according to claim 7, wherein said determining comprises fractionating said sample into at least two fractions in manner sufficient to separate 80 kDa proteins from 37 kDa proteins.

10. The method according to claim 9, wherein said method further comprises assaying said fractions comprising the 80 kDa and 37 kDa proteins for the presence of RNAse L proteins.

11. A method of characterizing multiple sclerosis disease activity in a subject, said method comprising:
   (a) identifying the presence of at least one symptom associated with multiple sclerosis in said subject;
   (b) obtaining a PBMC derived sample from said subject;
   (c) determining the ratio of 80 KDa RNAse L to 37 KDa RNAse L in said sample; and
   (d) using said ratio to characterize MS disease activity in said subject.

12. The method according to claim 11, wherein said determining comprises fractionating said sample into at least two fractions in manner sufficient to separate 80 kDa proteins from 37 kDa proteins.

13. The method according to claim 12, wherein said method further comprises assaying said fractions comprising the 80 kDa and 37 kDa proteins for the presence of RNAse L proteins.

14. A kit for use in characterizing multiple sclerosis disease activity in a subject, said kit comprising:
   (a) means for determining the relative amounts of high molecular weight and low molecular RNAse L proteins in a subject derived sample; and
   (b) a medium comprising reference information relating relative amounts of high and low molecular weight RNAse L proteins to multiple sclerosis.

15. The kit according to claim 14, wherein said kit further comprises means for obtaining a sample from said subject.

16. The kit according to claim 14, wherein said kit further comprises at least one reagent employed in an oligoclonal CSF assay.

17. A kit for use in characterizing multiple sclerosis disease activity in a subject, said kit comprising:
   (a) means for determining the relative amounts of high molecular weight and low molecular RNAse L proteins in a subject derived sample; and
   (b) a medium comprising reference information relating relative amounts of high and low molecular weight RNAse L proteins to multiple sclerosis, wherein said kit further comprises instructions for practicing the method of claim 1.

18. A kit for use in characterizing multiple sclerosis disease activity in a subject, said kit comprising:
   (a) means for determining the ratio of high molecular weight and low molecular proteins having RNAse L activity in a subject derived sample;
   (b) at least one reagent employed in an oligoclonal CSF assay; and
   (c) instructions for practicing the method of claim 1.

* * * * *